(12) United States Patent
Barklund (10) Patent No.: US 12,422,436 B2
(45) Date of Patent: Sep. 23, 2025

(54) WEEDING MECHANISM AND A WEEDING VEHICLE INCLUDING THE WEEDING MECHANISM

(71) Applicant: EKOBOT AB, Västerås (SE)

(72) Inventor: Albin Barklund, Västerås (SE)

(73) Assignee: EKOBOT AB, Västerås (SE)

( * ) Notice: Subject to any disclaimer, the term of this patent is extended or adjusted under 35 U.S.C. 154(b) by 745 days.

(21) Appl. No.: 17/836,478

(22) Filed: Jun. 9, 2022

(65) Prior Publication Data
US 2022/0394912 A1    Dec. 15, 2022

(30) Foreign Application Priority Data
Jun. 10, 2021 (EP) .................................. 21178793

(51) Int. Cl.
*A01B 39/18* (2006.01)

(52) U.S. Cl.
CPC .................................. *A01B 39/18* (2013.01)

(58) Field of Classification Search
CPC ......... A01B 39/00; A01B 39/02; A01B 39/06; A01B 39/12; A01B 39/18; A01B 39/19; A01B 63/111
USPC .................................................... 171/56, 62
See application file for complete search history.

(56) References Cited

U.S. PATENT DOCUMENTS

| | | | |
|---|---|---|---|
| 2008/0217034 A1* | 9/2008 | de Bree | A01B 45/023 172/21 |
| 2015/0282419 A1* | 10/2015 | Deutschle | A01B 39/20 172/101 |
| 2017/0251589 A1 | 9/2017 | Tippery et al. | |
| 2021/0022282 A1 | 1/2021 | Wallach et al. | |

FOREIGN PATENT DOCUMENTS

| | | | | |
|---|---|---|---|---|
| CN | 101707992 A | 5/2010 | | |
| CN | 106889052 A | 6/2017 | | |
| CN | 107690280 A | 2/2018 | | |
| CN | 109511356 A | 3/2019 | | |
| DE | 4323315 C2 * | 8/1996 | ......... | A01B 45/023 |
| EP | 3811748 A1 | 4/2021 | | |
| RU | 2703092 C1 | 10/2019 | | |

* cited by examiner

Primary Examiner — Christopher J Sebesta
Assistant Examiner — Evan A Bregel
(74) Attorney, Agent, or Firm — Dilworth & Barrese, LLP; Michael J. Musella, Esq.

(57) ABSTRACT

The present invention relates to a weeding mechanism (1) for an autonomous weeding vehicle, and a weeding vehicle including the weeding mechanism. The weeding mechanism comprises a first shaft (3), a second shaft (5) arranged spaced apart from the first shaft (3), a first sledge (7) linearly movable along the first shaft (3), a second sledge (9) linearly movable along the second shaft (5), first and second actuators (11, 13) arranged to independently move the first and second sledges (7, 9) along the first and second shafts (3, 5) respectively, a first arm (15) pivotably connected to the first sledge (7), a second arm (17) pivotably connected to the second sledge (9) and pivotably connected to the first arm (15), and a weeding tool (2) operatively connected to at least one of the first and second arms (15, 17).

16 Claims, 5 Drawing Sheets

WEEDING MECHANISM AND A WEEDING VEHICLE INCLUDING THE WEEDING MECHANISM

TECHNICAL FIELD

The present invention relates to a weeding mechanism for an autonomous weeding vehicle. The present invention also relates to a weeding vehicle for performing automatic weeding using the weeding mechanism. The invention relates to the technical field of agricultural machinery applications.

BACKGROUND

Autonomous weeding vehicles, also named robot weeders, are used to automatically remove weeds during the seedling stage of crops. Such weeding vehicles may comprise a movable platform, a drive mechanism for driving the platform, sensors for detecting the weed plants, and a weeding mechanism connected to the platform and comprising a weeding tool adapted to carry out a weeding action on the detected weed plants. The removal of the weed plants can be made in different ways. It is common to use chemical weeding. However, a disadvantage of chemical weeding is that the herbicide is wasteful and easily pollutes the environment. Mechanical weeding, such as cutting, is better for the environment. There exist different types of cutting tools for weeding vehicles.

CN101707992 discloses a weeding robot comprising an inter-row cutting mechanism arranged under the trolley, and an in-row weeding mechanism. The inter-row cutting mechanism comprises a first weeding mechanism that removes the weed below the trolley during traveling of the trolley. The in-row weeding mechanism comprises a weed cutting roller protruding from the trolley. The outer surface of the weed cutting roller has a blade edge rotating at high speed and the weed are cut due to the high-speed rotation of the roller. The inter-row cutting mechanism comprises two spaced apart rotating cylindrical saw discs. The rotating saw discs are moved between two crops in the row while removing the weed between the crops in the row. A problem with the rotating saw discs is that they will stir the soil when they are moved along the row of crops. This causes stirring of weed seed into the soil, and consequently stimulates growing of the weed. Another problem is that the stirring discs may harm the crop plants if the weed plant is growing close to a crop plant.

CN109511356 discloses a weeding vehicle comprising a robotic arm movable in multiple degrees of freedom and holding a cutting tool in the form of a rotating disc. A disadvantage with this solution is that a robot arm movable in many degrees of freedom is expensive and it is complicated to control the motion of robot arm, which requires extensive robot programming.

EP3811748 discloses a weeding mechanism including an actuator adapted to upon activation linearly move a cutting tool in a forth and back motion relative to the platform. The weeding mechanism comprises at least one horizontal shaft arranged movable relative the platform, and a vertical distance element attached to one end of the horizontal shaft. The cutting tool is attached to a lower end of the vertical distance element. The actuator is arranged to move the horizontal shaft along its axis so that the cutting tool is moved in a linear motion relative to the platform.

SUMMARY

It is an aim of the present invention to at least partly overcome the above problems, and to provide an improved weeding mechanism for an autonomous weeding vehicle.

The weeding mechanism comprises
a first shaft,
a second shaft arranged spaced apart from the first shaft,
a first sledge linearly movable along the first shaft,
a second sledge linearly movable along the second shaft,
first and second actuators arranged to independently move the first and second sledges along the first and second shafts respectively,
a first arm pivotably connected to the first sledge,
a second arm pivotably connected to the second sledge and pivotably connected to the first arm, and
a weeding tool operatively connected to at least one of the first and second arms.

This weeding mechanism makes it possible to move the weeding tool in 2 degrees of freedom. Thus, it is possible to execute different types of cutting sequences in two dimensions. The weeding tool can be controlled in a vertical direction as well as a horizontal direction. Thus, it is possible to reach the weed plant without touching the soil and by that avoid stirring the soil.

The first actuator is arranged to move the first sledge up and down along the first shaft, and the second actuator is arranged to move the second sledge up and down along the second shaft. The position of the weeding tool depends on the positions of the first and second sledges. The motions of the weeding tool are controlled by controlling the linear motions of the two sledges along the shafts. Thus, it is rather simple to control the motions of the weeding tool, which simplifies the programming of the weeding mechanism. The motions of the first and second sledges are controlled by the two actuators. Each of the first and second sledges can be moved independently up and down along the first and second shafts. The combination of the motions of the sledges and the pivotal arrangement of the first and second arms allows the weeding tool to perform an arbitrary motion within a 2-dimensional working area.

The weeding mechanism according to the invention is simple, and costs significantly less than a robotic arm movable in multiple degrees of freedom. Further, the weeding mechanism can rapidly move the weeding tool with high precision.

The weeding tool can be any type of weeding tool, such as a cutting tool, a laser, or a burner. The weeding mechanism is particularly suitable for moving a cutting tool in a cutting motion.

The weeding tool can be directly or indirectly connected to at least one of the first and second arms.

According to an embodiment of the invention, each of the first and second actuators comprises a linear motor and a drive belt. The combination of a linear motor and a drive belt achieves a high-speed weeding mechanism and makes it possible to carry fast motions with the weeding tool. Typically, the weeding tool can carry out about 6-7 cutting sequences per second.

According to an embodiment of the invention, the motor is a brushless DC motor.

According to an embodiment of the invention, the drive belt is a timing belt. A timing belt is a tooth belt with teeth on an inside surface.

According to an embodiment of the invention, the first and second shafts define a plane, and the first and second arms are arranged so that the weeding tool performs a motion in parallel with the plane when the first sledge and the second sledge are moved along the first and second shafts. Thus, the weeding tool can be moved vertically as well as horizontally in a plane defined by the first and second shafts.

According to an embodiment of the invention, the first and second arms are arranged so that the weeding tool can be moved to a left side of the first and second shafts as well as to a right side of the first and second shafts in the plane. Thus, the weeding tool can carry out weeding actions on both sides of the weeding mechanism.

According to an embodiment of the invention, the weeding tool has a cutting edge extending perpendicular to the plane defined by the first and second shafts. In this embodiment, the weeding tool is a cutting tool. The cutting edge is moved in a direction in parallel with the plane upon moving the first and second sledges.

According to an embodiment of the invention, the first and second arms are arranged so that the cutting edge can perform a linear motion in a first direction parallel with the plane when the first sledge and the second sledge are moved relative each other along the first and second shafts. Suitably, the first direction is a horizontal direction. This is advantageous since is allows the cutting tool to perform a linear motion during cutting of the weed plant.

According to an embodiment of the invention, the first and second arms are arranged so that the cutting edge can perform a linear motion in a second direction in parallel with the plane when the first sledge and the second sledge are synchronously moved along the first and second shafts. Suitably, the second direction is a vertical direction. This makes it possible to lower and raise the cutting tool before and after the cutting, and by that avoid stirring of weed seed into the soil.

According to an embodiment of the invention, the first arm is pivotably connected to the first sledge so that the first arm can perform a pivotal movement with respect to the first shaft about a first rotational axis, the second arm is pivotably connected to the second sledge so that the second arm can perform a pivotal movement with respect to the second shaft about a second rotational axis, the second arm is pivotably connected to the first arm so that the second arm can perform a pivotal movement with respect to the first arm about a third rotational axis, wherein the first, second and third rotational axes are parallel and perpendicular to a plane defined by the first and second shafts.

According to an embodiment of the invention, the weeding tool is attached to the first arm, and the second arm is pivotally connected to the first arm.

According to an embodiment of the invention, the weeding tool is attached to a lower end of the first arm.

According to an embodiment of the invention, the second arm is connected to the first arm at a distance from the lower end of the first arm. Preferably, the distance is at least 30 mm, preferably at least 50 mm, and most preferably at least 100 mm. Thus, the width of the lower end of the weeding mechanism, which is connected to the weeding tool, is reduced compared to having the second arm attached to the lower end of the first arm. The reduced width of the lower end of the weeding mechanism makes it possible for the weeding tool to enter between two seed plants close to each other without causing damage to the seed plants.

According to an embodiment of the invention, the width of the first arm in a direction perpendicular to the plane defined by the first and second shafts, is less than 30 mm, preferably less than 25 mm and most preferably less than 20 mm. A thinner arm makes it easier for it to enter between two seed plants close to each other without causing damage to the seed plants.

According to an embodiment of the invention, the width of the weeding tool in a direction perpendicular to the plane defined by the first and second shafts is less than 30 mm, preferably less than 25 mm and most preferably less than 20 mm. A thinner tool makes it easier for it to enter between two seed plants close to each other without causing damage to the seed plants.

According to an embodiment of the invention, an upper end of the second arm is pivotably connected to the second sledge and a lower end of the second arm is pivotably connected to the first arm at a distance from the lower end of the first arm.

According to an embodiment of the invention, an upper end of the first arm is pivotably connected to the first sledge and the weeding tool is connected to the lower end of the first arm.

According to an embodiment of the invention, each of the first and second actuators comprises a motor with a variable speed having a rotary shaft arranged to rotate in two opposite directions.

According to an embodiment of the invention, the weeding mechanism further comprises:
 a third shaft arranged in parallel and spaced apart from the first shaft,
 a fourth shaft arranged in parallel and spaced apart from the second shaft,
 a third sledge arranged linearly movable along the third shaft and connected to the first sledge so that the first and third sledges are moved interdependently, and
 a fourth sledge arranged linearly movable along the fourth shaft and connected to the second sledge so that the fourth and second sledges are moved interdependently, wherein the first arm is pivotably connected to the first and third sledges, and the second arm is pivotably connected to the second and fourth sledges.

This embodiment of the invention is more robust and can stand the high speed of the weeding tool.

Another aim of the present invention is to provide an improved autonomous weeding vehicle.

The weeding vehicle comprises a weeding mechanism according to the invention, and a weeding control unit for controlling the first and second actuators so that the weeding tool carries out a weeding action.

According to an embodiment of the invention, the weeding vehicle comprises one or more sensors adapted to detect weed plants, and the weeding control unit controls the first and second actuators so that the weeding tool carries out weeding actions based upon output from sensors.

According to an embodiment of the invention, the weeding mechanism is adapted to carry out a weeding action upon receiving an activation command, and the weeding control unit is configured to send activation commands to the weeding mechanism.

According to an embodiment of the invention, the weeding vehicle comprises two or more weeding mechanisms which can operate independently of each other. Thus, it is possible to simultaneously carry out weeding of two or more rows of weeding plants.

BRIEF DESCRIPTION OF THE DRAWINGS

The invention will now be explained more closely by the description of different embodiments of the invention and with reference to the appended figures.

DETAILED DESCRIPTION

Aspects of the present disclosure will be described more fully hereinafter with reference to the accompanying drawings. The weeding mechanism can, however, be realized in many different forms and should not be construed as being limited to the aspects set forth herein. Like numbers in the drawings refer to like elements throughout.

The terminology used herein is for the purpose of describing particular aspects of the disclosure only and is not intended to limit the invention. As used herein, the singular forms "a", "an" and "the" are intended to include the plural forms as well, unless the context clearly indicates otherwise.

Figure 1:
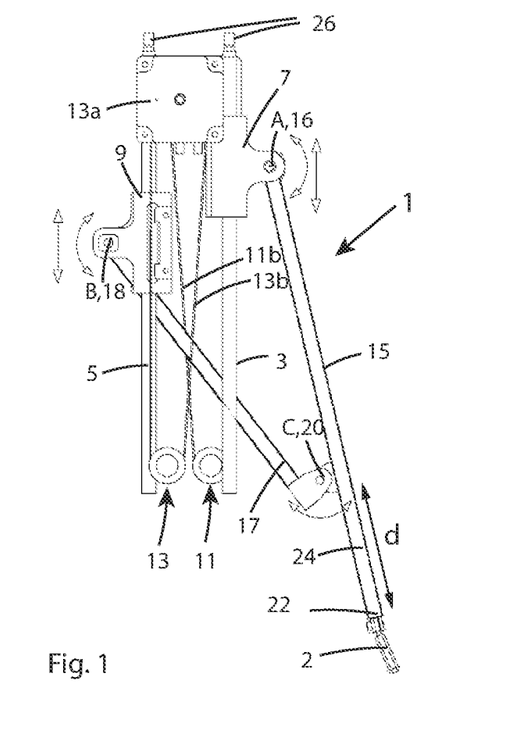
FIG. 1 shows an example of a weeding mechanism according to the invention.

FIG. 1 shows an example of a weeding mechanism 1 according to the invention. The weeding mechanism comprises a weeding tool 2, and a mechanism for moving the weeding tool comprising a first shaft 3, and a second shaft 5 arranged spaced apart from the first shaft 3. Preferably, the first and second shafts 3, 5 are arranged in parallel. Suitably, the first and second shafts 3, 5 are vertically arranged when the weeding mechanism is mounted on a weeding vehicle. Alternatively, the shafts can be arranged with a small angle between them. The first and second shaft define a plane, which preferably is vertical when the weeding mechanism is mounted on the weeding vehicle. Suitably, the shafts 3, 5 are made of metal, for example, stainless steel.

The weeding mechanism 1 further comprises a first sledge 7 linearly movable along the first shaft 3, and a second sledge 9 linearly movable along the second shaft 5. The sledges can be moved up as well as down along the shafts 3, 5. Each of the first and second sledges 7, 9 is provided with a through hole for receiving one of the shafts 3, 5. Preferably, the through holes are provided with bearings, such as slide bearings, to reduce the friction between the shafts and the sledges during the motions of the sledges along the shafts. The sledges 7, 9 are, for example, made of a plastic material or metal, such as aluminium.

The weeding mechanism 1 comprises a first actuator 11 arranged to move the first sledge 7 along the first shaft 3, and a second actuator 13 arranged to move the second sledge 9 along the second shaft 5. The first and second actuators 11, 13 are arranged so that the first and second sledges 7, 9 can be moved independently of each other up and down along the shafts. In the illustrated example, each of the first and second actuators 11, 13 comprises a motor 11a, 13a, and a drive belt 11b, 13b. Preferably, each of the first and second actuators 11, 13 comprises a linear motor. A linear motor is an electric motor arranged to produce a linear motion instead of a rotating motion. More preferably, each of the first and second actuators 11, 13 comprises a brushless linear motor, for example, a brushless DC motor, which can perform high performance positioning of the sledges 7, 9 with respect to the shafts 3, 5. For example, the drive belts 11b, 13b are timing belts. A timing belt is usually a toothed belt with teeth on an inside surface. Alternatively, the actuators 11, 13 may include timing chains, cambelts, or gear racks.

The weeding mechanism 1 further comprises a first arm 15 pivotably connected to the first sledge 7 so that the first arm can perform a pivotal movement with respect to the first shaft 3 about a first rotational axis A, and a second arm 17 pivotably connected to the second sledge 9 so that the second arm 17 can perform a pivotal movement with respect to the second shaft 5 about a second rotational axis B. The first and second rotational axes A, B are parallel, and perpendicular to the plane defined by the first and second shafts 3, 5. The first rotational axis A extends through a joint 16 between the first arm 15 and the first shaft 3. The second rotational axis B extends through a joint 18 between the second arm 17 and the second shaft 5. Preferably, an upper end of the first arm 15 is pivotably connected to the first sledge 7 and an upper end of the second arm 17 is pivotably connected to the second sledge 9. A lower end of the second arm 17 is pivotably connected to the first arm 15 so that the second arm 17 can perform a pivotal movement with respect to the first arm 15 about a third rotational axis C. The third rotational axis C is parallel to the first and second rotational axes A, B, and consequentially perpendicular to the plane defined by the first and second shafts 3, 5. The third rotational axis C extends through a third joint 20 between the first and second arms 15, 17. Due to the fact that the first, second and third rotational axes A, B, C are perpendicular to the plane defined by the first and second shafts 3, 5, the weeding tool will perform a motion in parallel with the plane defined by the first and second shafts when the first and second sledges 7, 9 are moved along the first and second shafts.

In the illustrated example, the weeding tool 2 is attached to a lower end 22 of the first arm 15, and the second arm 17 is pivotally connected to the first arm 15 at a distance d from the lower end of the first arm 15. For example, the distance d is at least 30 mm, preferably the distance d is at least 50 mm, and most preferably at least 100 mm. For example, the distance d is 150 mm. A lower part of the first arm 15, defined between the lower end 22 of the first arm and the connection to the second arm 17, functions as a tool holder 24. Preferably, the tool holder 24 is as thin as possible so that the tool holder can be moved between two weed plants that are close to each other without causing any harm on the weed plants. Preferably, the width w1 of the tool holder in a direction perpendicular to the plane defined by the first and second shafts 3, 5 is less than 30 mm, preferably less than 25 mm, and most preferably less than 20 mm. For the same reason, the width w2 of the weeding tool in a direction perpendicular to the plane defined by the first and second shafts 3, 5 should be as small as possible. For example, the width of the weeding tool in the direction perpendicular to the plane defined by the first and second shafts 3, 5 is less than 30 mm, preferably less than 25 mm, and most preferably less than 20 mm.

Figure 4:
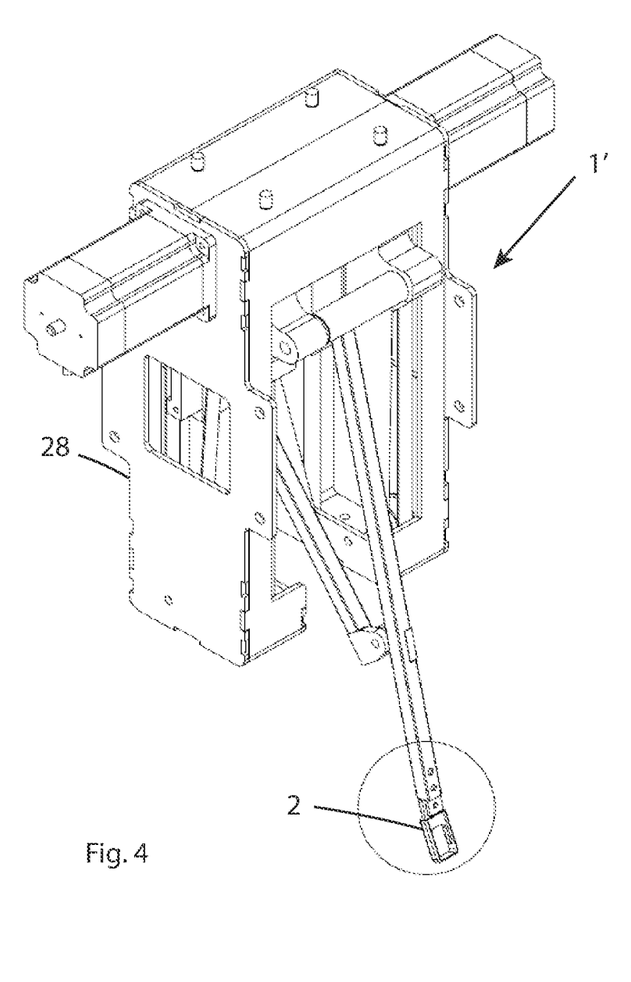
FIG. 4 shows the weeding mechanism arranged in a housing.

The weeding mechanism is also provided with attaching members 26 for attaching the weeding mechanism 1 to a housing 28, shown in FIG. 4. In this example, the attaching members 26 are threaded upper parts of the shafts 3, 5.

The weeding mechanism 1 is based on a 2d-delta design. The two motors 11a, 13a are driving the two belts 11b, 13b that move the two sledges 7, 9 up and down the two shafts 3, 5, respectively. The sledges 7, 9 are then connected to the joints 16, 18 of the two arms 15, 17. This creates a weeding mechanism with 2 degrees of freedom capable of executing arbitrary cutting sequences in 2 dimensions.

Figure 2:
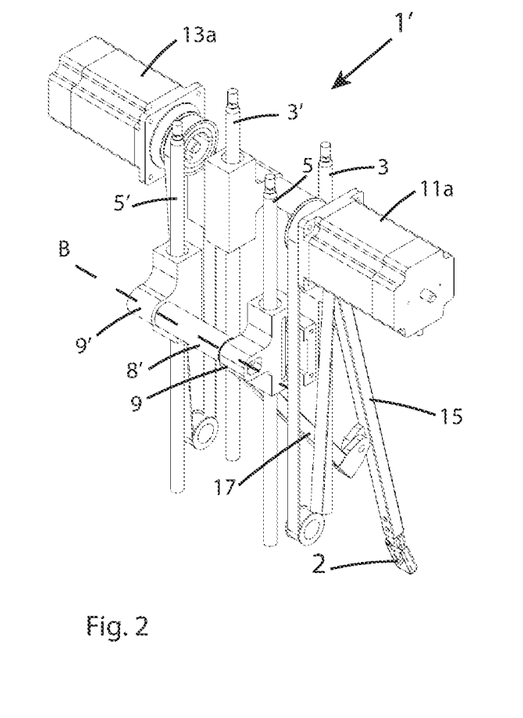
FIGS. 2 and 3 show another example of a weeding mechanism according to the invention shown in two perspective views.
Figure 3:
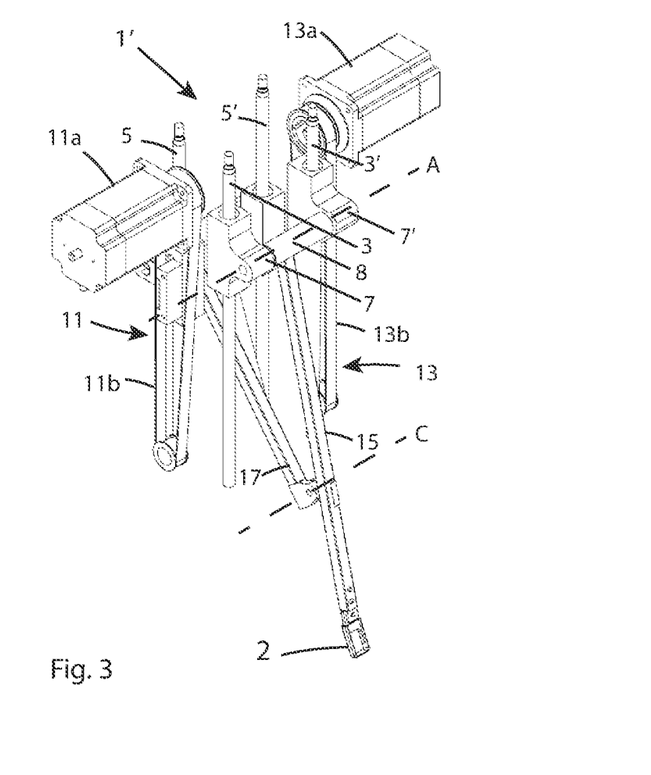

FIGS. 2 and 3 show another example of a weeding mechanism 1' according to the invention. FIG. 2 shows the weeding mechanism 1' in a left perspective view. FIG. 3 shows the weeding mechanism in a right perspective view. The weeding mechanism 1' comprises a third shaft 3' arranged in parallel and spaced apart from the first shaft 3, and a fourth shaft 5' arranged in parallel and spaced apart from the second shaft 5. The weeding mechanism 1' further comprises a third sledge 7' arranged linearly movable along the third shaft 3' and a fourth sledge 9' arranged linearly movable along the fourth shaft 5'. The third sledge 7' is connected to the first sledge 7 so that the first and third sledges 7, 7' are moved interdependently. This means that when one of the first and third sledges 7, 7' are moved along one of the first and third shafts, the other sledge will perform a corresponding motion along the other shaft. The second and fourth sledges 9, 9' are moved interdependently, which means that the second and fourth sledges 9, 9' perform corresponding motions when one of the sledges is moved.

The weeding mechanism 1' comprises a first rotary shaft 8 rotatably connected between the first and third sledges 7, 7'. The first sledge 7 comprises a space for receiving one end of the first rotary shaft 8, and the third sledge 7' comprises a corresponding space for receiving the other end of the first rotary shaft 8. The first rotary shaft 8 is arranged rotatable with respect to the first and third sledges 7, 7' about the first rotational axis A. The weeding mechanism 1' comprises a second rotary shaft 8' rotatably connected between the second and fourth sledges 9, 9'. The second sledge 9 comprises a space for receiving one end of the second rotary shaft 8', and the fourth sledge 9' comprises a corresponding space for receiving the other end of the second rotary shaft 8'. The second rotary shaft 8 is arranged rotatable with respect to the second and fourth sledges 9, 9' about the second rotational axis B.

The first arm 15 is attached to the first rotary shaft 8 and the second arm 17 is attached to the second rotary shaft 8'. The first arm 15 is pivoted about the first rotational axis A by moving the first and third sledges 7, 7' along the first and third shafts 3, 3' and with respect to the second and fourth sledges 9, 9'. The second arm 17 is pivoted about the second rotational axis B by moving the second and fourth sledges 9, 9' along the second and fourth shafts 5, 5' and with respect to the first and third sledges 7, 7'. The first actuator 11 is arranged to simultaneously move the first and third sledges 7, 7' along the first and third shafts 3, 3', and the second actuator 13 is arranged to simultaneously move the second and fourth sledges 9, 9' along the second and fourth shafts 5, 5'. This embodiment of the invention is more robust and can stand high speed of the weeding tool.

FIG. 4 shows the weeding mechanism 1' arranged in a housing 28.

Figure 5:
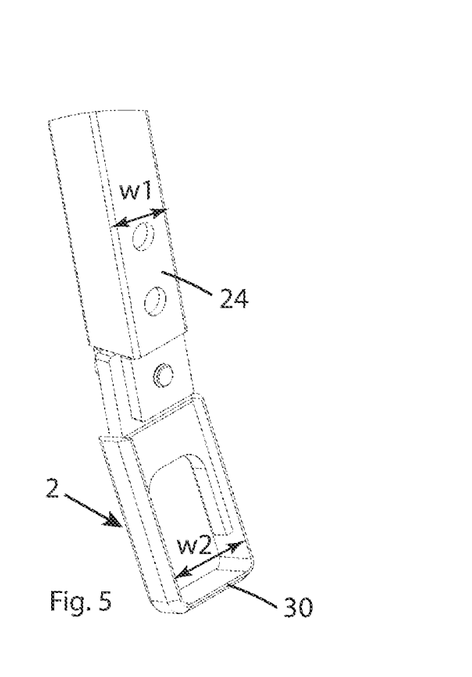
FIG. 5 shows an example of a weeding tool.

The weeding tool 2 can be designed in many ways. FIG. 5 shows an example of a weeding tool 2. The weeding tool 2 is a cutting tool having a cutting edge 30 extending perpendicular to the plane defined by the first and second shafts 3, 5. Thus, the arms 15, 17 will move the cutting edge 30 in a direction in parallel with the plane defined by the first and second shafts upon moving the first and second sledges. In the illustrated example, the weeding tool comprises a U-shaped part. A lower portion of the U-shaped part comprises the cutting edge 30. The U-shaped part is fixedly or removably attached to the lower end 22 of the first arm 15. Preferably, the weeding tool 2 is made of metal, such as stainless steel. The weeding tool 2 is designed to cut the roots of the weed plats and/or pull the weed plant out of the ground.

Figure 6A:
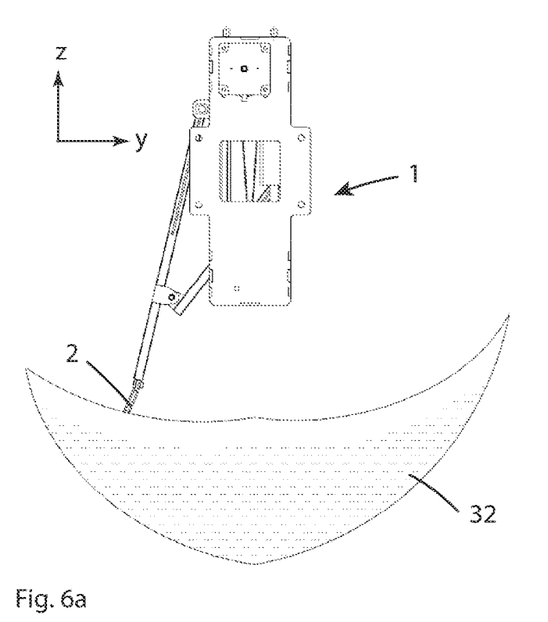
FIGS. 6a-b illustrate the working area of the weeding mechanism.
Figure 6B:
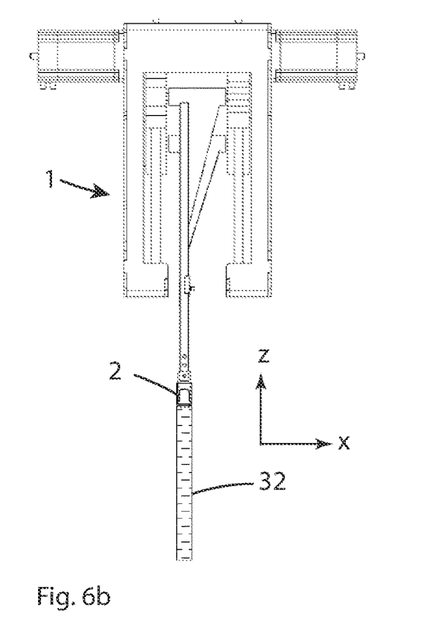

FIGS. 6a-b illustrate the working area 32 of the weeding mechanism. FIG. 6a illustrates the working area in a z-y plane, which is the plane defined by the first and second shafts. As seen from FIG. 6a, the weeding tool can reach both sides of the housing of weeding mechanism. The first and second arms 15, 17 are arranged so that the weeding tool 2 can be moved to a left side of the first and second shafts as well as to a right side of the first and second shafts in the plane. Thus, the weeding tool can carry out weeding actions on both sides of the weeding mechanism. FIG. 6b illustrates the working area 32 in a z-x plane, i.e. a plane perpendicular to the plane defined by the first and second shafts. As seen from FIG. 6b, the working area in the z-x plane corresponds to the width w2 of the weeding tool.

The first and second arms 15, 17 are arranged so that the weeding tool can perform a linear motion in an y-direction when the first sledge and the second sledge are moved relative each other along the first and second shafts. This is advantageous since is allows the cutting tool to perform a linear motion during cutting of the weed plant.

The first and second arms 15, 17 are arranged so that the weeding tool can perform a linear motion in a z-direction when the first sledge and the second sledge are synchronously moved along the first and second shafts. This makes it possible to lower and raise the cutting tool before and after the cutting, and by that avoid stirring of weed seed in the soil.

Figure 7A:
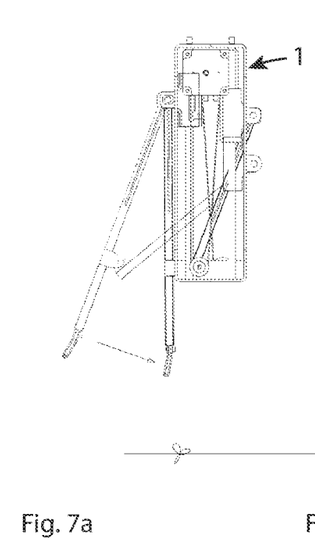
FIGS. 7a-d illustrate the use of the cutting mechanism for removing a weed plant.
Figure 7B:
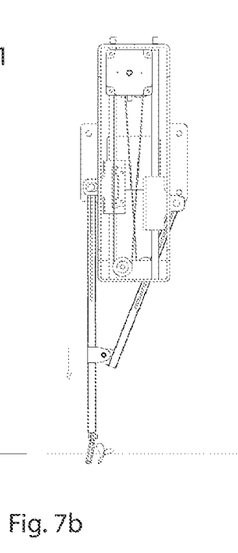
Figure 7C:
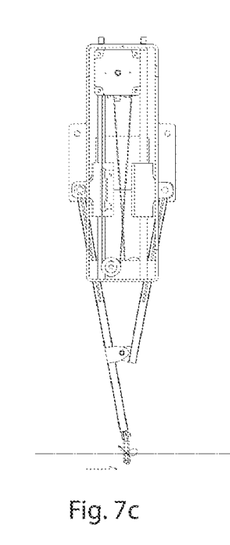
Figure 7D:
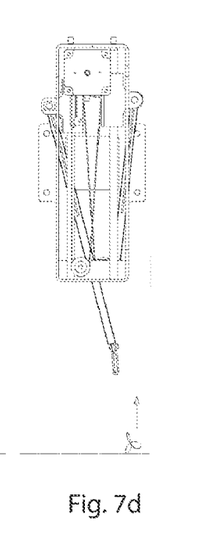

FIGS. 7a-d illustrate an example of how to use of the cutting mechanism for removing a weed plant. When a weed plant has been detected by the weeding vehicle, the weeding tool 2 is moved from its current position to a position close to the weed plant, above the soil, and at one side of the weed plant, as shown in FIG. 7a. The weeding mechanism is now ready to execute a strike. The weeding tool 2 is lowered in a vertical direction at one side of the weed plant until the tool 2 reaches the soil. Optionally, the tool can be lowered about 2 cm into the soil, as shown in FIG. 7b. The tool 2 is linearly moved in a horizontal direction so that the cutting edge of the tool 2 cuts the roots of the weed plant and/or pulls the weed plant out of the ground, as shown in FIG. 7c. In a last step, the tool 2 is returned to an idle position by linearly moving the tool 2 in the vertical direction, as shown in FIG. 7d.

Figure 8:
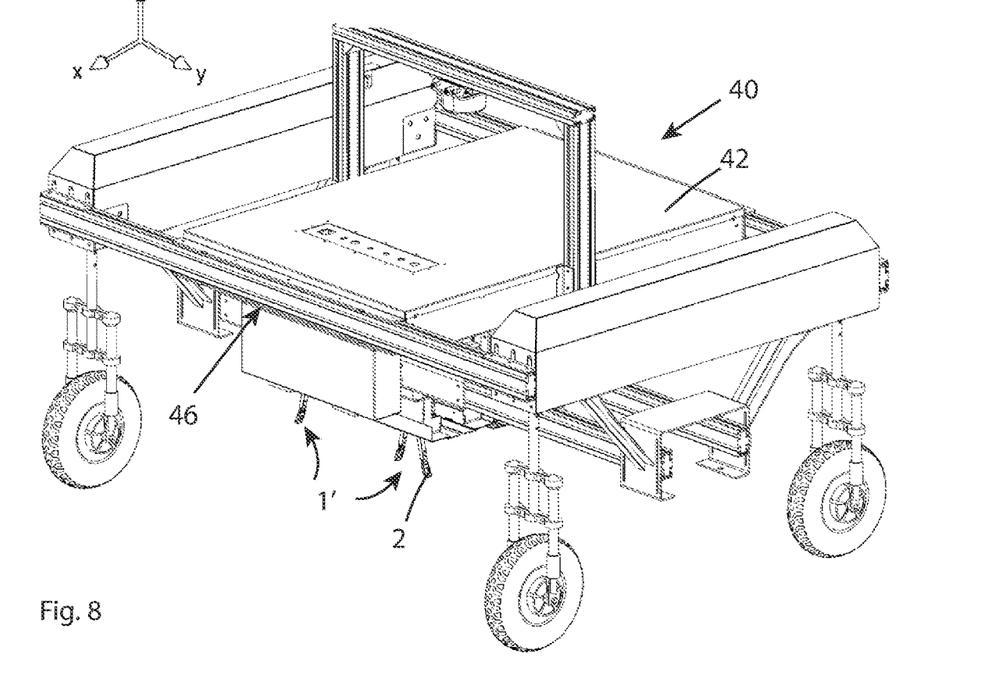
FIG. 8 shows in a perspective view an example of a weeding vehicle including a weeding mechanism.
Figure 9:
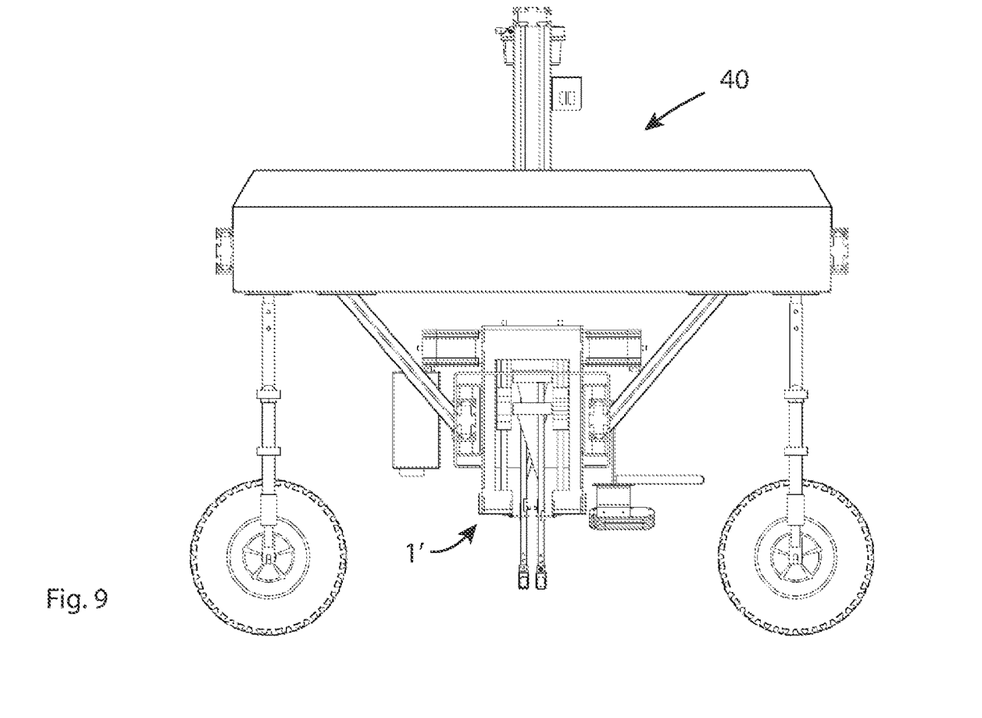
FIG. 9 shows the weeding vehicle in a front view.
Figure 10:
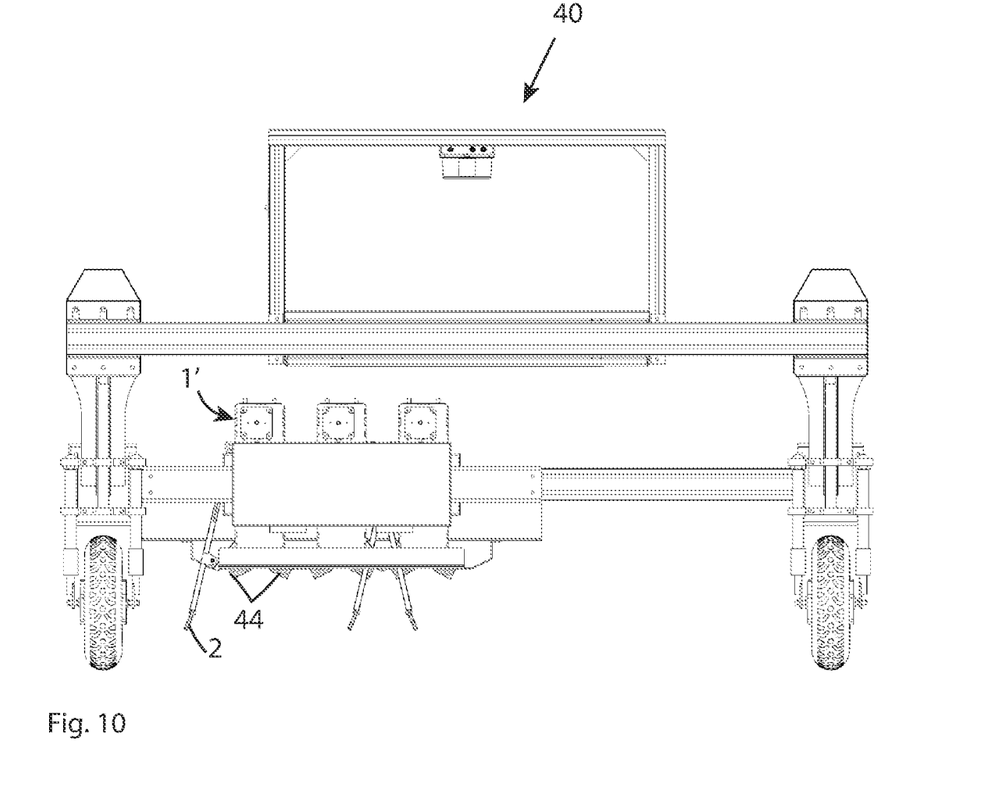
FIG. 10 shows the weeding vehicle in a side view.

FIG. 8 shows in a perspective view an example of a weeding vehicle 40 including a weeding mechanism. FIG. 9 shows the weeding vehicle in a front view, and FIG. 10 shows the weeding vehicle in a side view. In the illustrated example, the weeding vehicle 40 comprises the weeding mechanism 1'. However, the weeding vehicle 40 can also comprise the weeding mechanism 1, or other embodiments of the weeding mechanism according to the invention. In this example, the weeding vehicle 40 comprises three weeding mechanisms 1' arranged spaced apart in an y-direction with respect to the vehicle 40 at a bottom side of the vehicle 40. However, the number of weeding mechanisms 1' can vary, between one or more than three. The vehicle 40 is moving in a x-direction and the tool 2 can be moved in the y-direction and in the z-direction with respect to the vehicle 40. For example, the weeding tool 2 is a cutting tool having a cutting edge 30 arranged substantially perpendicular to the y direction to be able to cut the weed plants during the movement of the cutting tool 2 in the y direction.

The weeding vehicle 40 further comprises a control unit 12 for controlling the weeding mechanism 1, 1'. The control unit 42 is adapted to control the first and second actuators 11, 13 so that the weeding tool 2 carries out a weeding action, for example, as illustrated in FIGS. 7a-d. The control unit 42 can also be adapted to determine when the weeding action is to be carried out and to generate an activation command when the weeding action shall start. The control unit 42 can be the same control unit used to perform vehicle functions, such as controlling the motions of the platform of the weeding vehicle. The control unit 42 comprises a data processing circuitry for controlling the weeding mechanism 1, 1' and memory for storing control programs for controlling the weeding mechanism to carry weeding actions. The memory can also be used for storing operating parameters for controlling the weeding mechanism. The memory may comprise two or more control programs including instructions for carrying out different types of weeding actions with the weeding tool. The data processing circuitry can be any suitable means for processing data, such as a computer, a CPU, and programmable circuits, such as FPGAs. The memory may, for example, comprise EPROM, EEPROM, flash memory, RAM, a solid-state disc drive, a hard disc drive, or any other memory type or combinations of memory types. The weeding action can be carried out by programming instructions stored in the memory and executed by the data processing circuitry. The control unit 42 controls the motions of sledges along the shafts by providing control signals to the motors 11a, 13a of the first and second actuators 11, 13, and by that controls the motions of the weeding tool 2.

The weeding vehicle 40 comprises sensors 44 adapted to detect weed plants, and the control unit 42 controls the first and second actuators so that the weeding tool carries out weeding actions based on output from the sensors. The number of sensors 44 may vary. In this example, each weeding mechanism 1' is provided with two sensors 44, as shown in FIG. 10.

The weeding vehicle 40 comprises a movable platform 46, and a drive mechanism for driving the platform 46. The platform 46 is provided with a plurality of wheels. The drive mechanism for driving the platform comprises a plurality of motors. The motors are, for example, electrical hub motors mounted on the wheels. The weeding mechanism 1, 1' is connected to the platform 46 for carrying out weeding of weed plants. The weeding control unit 42 is configured to send activation commands to the weeding mechanism. The weeding mechanism 1, 1' is adapted to carry out a weeding action upon receiving an activation command from the weeding control unit 42. Preferably, the weeding tool 2 has a fixed position relative to the platform 46 in the x-direction. Thus, the current position of the tool in the x-direction is known if the current position of the platform is known. The purpose of the weeding action is to remove or kill the weed plant. Different types of weeding tools 20 can be used. For example, the weeding tool 2 can be a cutting tool, a laser, a spraying nozzle, or a gas nozzle. The weeding action to be carried out upon receiving the activation command depends on the type of the weeding tool. For example, if the weeding tool is a cutting tool, the cutting tool is moved to the weed plant to be removed upon receiving the activation command.

The weeding vehicle 40 comprises a plant detection system adapted to detect weed plants at a distance ahead of the weeding tool 2 while the platform 46 is moving in the x-direction. The x-direction is the direction of travel of the platform. The plant detection system comprises one or more sensors 44 arranged in connection to the platform for identifying the plants. For example, the sensor 44 is a camera taking images in the form of photos of the ground in front of the weeding tool 2. Alternatively, the sensor 44 can be an energy reflection analysis sensor such as a laser sensor.

For example, the plant detection system comprises a vision system arranged to obtain the images from the sensors 44. The vision system is adapted to detect the plants and to determine the positions of the detected plants based on the received images. The weeding control unit 42 comprises a data processing circuitry configured to obtain information on the speed of the platform from the drive mechanism, to obtain the positions of the detected weed plants, the current position of the tool, and the speed of the platform, and to send an activation command to the weeding mechanism when the tool has reached an optimal tool activation position. The plant detection system and the control unit 42 may share the same data processing circuitry.

The present invention is not limited to the embodiments disclosed but may be varied and modified within the scope of the following claims. For example, the length of the arms may vary. The sledges can be designed in different ways. The tool can be directly connected to the first arm and/or the first arm, or indirectly connected to the first arm and/or the first arm, for example via, an extension part.

REFERENCE LIST 1. weeding mechanism
1'. weeding mechanism
2. weeding tool
3. first shaft
3'. third shaft
5. second shaft
5'. fourth shaft
7. first sledge
7'. third sledge
8. first rotary shaft
8' second rotary shaft
9. second sledge
9'. fourth sledge
11. first actuator
11a. motor
11b. drive belt
13. second actuator
13a. motor
13b. drive belt
15. first arm
16. first joint
17. second arm
18. second joint
20. third joint
22. lower end of the first arm
24. tool holder
26. attaching members
28. housing
30. cutting edge
32. working area
40. weeding vehicle
42. control unit
44. sensor
46 movable platform
A, B, C first, second, and third rotational axes
d. length of the tool holder
w1. width of the tool holder
w2. width of the tool

The invention claimed is:

1. A weeding mechanism (1; 1') for an autonomous weeding vehicle, wherein the weeding mechanism comprises:
a first shaft (3), a second shaft (5) arranged spaced apart from the first shaft (3), a first sledge (7) linearly movable along the first shaft (3), a second sledge (9) linearly movable along the second shaft (5), first and second actuators (11, 13) arranged to independently move the first and second sledges (7, 9) along the first and second shafts (3, 5) respectively, a first arm (15) pivotably connected to the first sledge (7), a second arm (17) pivotably connected to the second sledge (9) and pivotably connected to the first arm (15), and a weeding tool (2) operatively connected to at least one of the first and second arms (15, 17).

2. The weeding mechanism according to claim 1, wherein each of the first and second actuators (11, 13) comprises a linear motor (11a, 13a) and a drive belt (11b, 13b).

3. The weeding mechanism according to claim 2, wherein said motors (11a, 13a) are brushless DC motors and the drive belts (11b, 13b) are timing belts.

4. The weeding mechanism according to claim 1, wherein the first and second shafts (3, 5) define a plane, and the first and second arms (15, 17) are arranged so that the weeding tool (2) performs a motion in parallel with said plane when the first and second sledge (7, 9) are moved along the first and second shafts (3, 5), respectively.

5. The weeding mechanism according to claim 4, wherein the weeding tool (2) has a cutting edge (30) extending perpendicular to said plane.

6. The weeding mechanism according to claim 5, wherein the first and second arms (15, 17) are arranged so that said cutting edge (30) can perform a linear motion in a first direction in parallel with said plane when the first sledge (7) and the second sledge (9) are moved relative each other along the first and second shafts (3, 5), and said cutting edge (30) can perform a linear motion in a second direction in parallel with said plane when the first sledge (7) and the second sledge (9) are synchronously moved along the first and second shafts (3, 5).

7. The weeding mechanism according to claim 1, wherein the first arm (15) is pivotably connected to the first sledge (7) so that the first arm (15) can perform a pivotal movement with respect to the first shaft (3) about a first rotational axis (A), the second arm (17) is pivotably connected to the second sledge (9) so that the second arm (17) can perform a pivotal movement with respect to the second shaft (5) about a second rotational axis (B), the second arm (17) is pivotably connected to the first arm (15) so that the second arm (17) can perform a pivotal movement with respect to the first arm (15) about a third rotational axis (C), and the first, second and third rotational axes (A, B, C) are arranged in parallel and perpendicular to a plane defined by the first and second shafts (3, 5).

8. The weeding mechanism according to claim 1, wherein the weeding tool (2) is attached to the first arm (15), and the second arm (17) is pivotally connected to the first arm (15).

9. The weeding mechanism according to claim 8, wherein the weeding tool (2) is attached to a lower end (22) of the first arm (15), and the second arm (17) is connected to the first arm (15) at a distance (d) from the lower end of the first arm.

10. The weeding mechanism according to claim 9, wherein said (d) distance is at least 30 mm.

11. The weeding mechanism according to claim 1, wherein the first and second shafts (3, 5) define a plane, and the width (w1) of the first arm (15) in a direction perpendicular to said plane is less than 30 mm.

12. The weeding mechanism according to claim 1, wherein the width (w2) of the weeding tool (2) in a direction perpendicular to said plane is less than 30 mm.

13. The weeding mechanism according to claim 1, wherein the weeding mechanism further comprises:

a third shaft (3') arranged in parallel and spaced apart from the first shaft (3), a fourth shaft (5') arranged in parallel and spaced apart from the second shaft (5), a third sledge (7') arranged linearly movable along the third shaft (3') and connected to the first sledge (7) so that the first and third sledges (7, 7') are moved interdependently, and a fourth sledge (9') arranged linearly movable along the fourth shaft (5') and connected to the second sledge (9) so that the second and fourth sledges (9, 9') are moved interdependently, wherein the first arm (15) is pivotably connected to the first and third sledges (7, 7'), and the second arm (17) is pivotably connected to the second and fourth sledges (9, 9').

14. A weeding vehicle (40) comprising the weeding mechanism (1, 1') according to claim 1, and a control unit (42) for controlling said first and second actuators (11, 13) so that the weeding tool (2) carries out a weeding action.

15. The weeding vehicle according to claim 14, wherein the weeding vehicle (40) comprises one or more sensors (44) adapted to detect weed plants, and the control unit (42) controls said first and second actuators (11, 13) so that the weeding tool (2) carries out weeding actions based on output from the one or more sensors (44).

16. The weeding vehicle according to claim 14, wherein weeding vehicle (40) comprises two or more of said weeding mechanisms (1, 1'), which can operate independently of each other.

* * * * *